(12) United States Patent
Hohenstein

(10) Patent No.: US 7,473,394 B2
(45) Date of Patent: Jan. 6, 2009

(54) SEPARATING VESSEL

(75) Inventor: Boyne Friedrich Hohenstein, Boksburg (ZA)

(73) Assignee: Innovative Met Products (PTY) Limited, Boksburg (ZA)

(*) Notice: Subject to any disclaimer, the term of this patent is extended or adjusted under 35 U.S.C. 154(b) by 388 days.

(21) Appl. No.: 10/534,759

(22) PCT Filed: Sep. 12, 2003

(86) PCT No.: PCT/ZA03/00132

§ 371 (c)(1),
(2), (4) Date: Dec. 6, 2005

(87) PCT Pub. No.: WO2004/044578

PCT Pub. Date: May 27, 2004

(65) Prior Publication Data

US 2006/0170139 A1    Aug. 3, 2006

(30) Foreign Application Priority Data

Nov. 14, 2002   (ZA) ................................... 02/9262

(51) Int. Cl.
*C22B 1/00*    (2006.01)
*F27D 3/15*    (2006.01)

(52) U.S. Cl. .................... 266/205; 266/227; 266/232; 432/262

(58) Field of Classification Search ............... 266/205, 266/227, 229, 232; 432/262, 263
See application file for complete search history.

(56) References Cited

U.S. PATENT DOCUMENTS 777,725 A * 12/1904 Fox ........................ 432/262
3,516,478 A * 6/1970 Dunn et al. ................ 266/227
4,769,066 A  9/1988 Eidem
6,074,598 A  6/2000 Koffron

FOREIGN PATENT DOCUMENTS

BE    695 996 A    9/1967
WO    02/04919 A   1/2002

OTHER PUBLICATIONS

International Search Report of PCT/ZA03/00132 mailed Dec. 29, 2003.
Examination Report in ARIPO Application No. AP/P/2005/003322, dated Mar. 14, 2008.
Examination Report in European Application No. 03 755 881.4-2122, dated Jun. 13, 2007.

* cited by examiner

*Primary Examiner*—Scott Kastler
(74) *Attorney, Agent, or Firm*—Nixon & Vanderhye P.C.

(57) ABSTRACT

The invention provides a separating vessel (10) suitable for use in the treatment of a mineral sample wherein a molten slag (11) is separated from a molten collector material (12) comprising a container defining an interior cavity (13) for receiving the molten materials (11, 12), an outlet aperture (14) leading from the interior cavity to the exterior of the container, and a separating surface (15) associated with the outlet aperture (14) which is shaped to cause droplets of flux (11*a*) to be carried along such surface, while droplets of collector material (12*a*) drip off such surface by the force of gravity.

11 Claims, 4 Drawing Sheets

SEPARATING VESSEL

This application is the US national phase of international application PCT/ZA2003/000132 filed 12 Sep. 2003, which designated the U.S. and claims priority to ZA 02/9262, filed 14 Nov. 2002, the entire contents of each of which are hereby incorporated by reference.

FIELD OF THE INVENTION

This invention relates to a separating vessel particularly suitable for, but not limited to, use in mineral sample analysis.

BACKGROUND TO THE INVENTION

In the field of fire assaying, mineral samples are mixed with a flux in a reaction vessel and fused to form a molten flux and molten collector material which collects a metal to be assayed. In conventional fire assay methods, the flux and collector material are caused to solidify and thereafter separated mechanically.

OBJECT OF THE INVENTION

It is accordingly an object of the present invention to provide a novel separating vessel suitable for separating molten slag from a molten collector material in a mineral sample analysis method such as a fire assay process.

SUMMARY OF THE INVENTION

According to the invention a separating vessel suitable for use in a mineral sample treatment method wherein a molten slag is separated from a molten collector material, comprises a container defining an interior cavity for receiving the molten materials, an outlet aperture leading from the interior cavity to the exterior of the container, and a separating surface associated with the outlet aperture which is shaped to cause droplets of flux to be carried along such surface, while droplets of collector material drip off such surface by the force of gravity.

In a preferred arrangement the separating surface is a downwardly directed concave surface. Such concave surface is preferably concentrically arranged relative to the outlet aperture.

Further according to the arrangement, the outlet aperture has dimensions such that the collector material passes through the aperture under the force of gravity, while the molten flux material is substantially prevented from passing through the outlet aperture.

Thus with the above arrangement, the majority of molten flux will be arrested at the outlet aperture, but a small portion which may pass through the outlet aperture, will be separated from the collector material by the separating surface. This could for example take place where the outlet aperture is gradually enlarged through use.

In a preferred arranged the outlet aperture will be disposed at low level in the interior cavity, and a slag outlet will be provided in the container spaced vertically upwardly from the outlet aperture, the arrangement being one wherein molten slag which overlies the collector material in the molten state will drain from the slag outlet during the process of draining the collector material through the outlet aperture. Molten slag which ultimately remains in the separating vessel after removal of the collector material can be removed from the vessel for example by tilting or inverting the vessel.

Also included separately within the scope of the invention is a method of separating molten collector material from molten slag suitable for use in the treatment of a mineral sample comprising the steps of:

provided the separating vessel of the invention;

introducing a mixture of molten slag and molten collector material into the vessel whereby the slag settles above the collector material as a result of density differentials;

draining the collector material through the outlet aperture under the force of gravity while the slag is substantially arrested by the outlet aperture;

further separating the collector material from the slag which has passed through the outlet aperture at the separating surface where at collector material runs vertically downwardly from the exit of the outlet aperture under the force of gravity while the slag is displaced laterally along the separating surface.

Further according to the invention the method includes the step of draining slag through the slag outlet. Preferably, slag will drain through the outlet during or prior to draining the collector material through the outlet aperture.

BRIEF DESCRIPTION OF THE DRAWINGS

The invention is further described in the preferred embodiment described hereunder purely by way of example with reference to the accompanying drawings wherein.

DETAILED DESCRIPTION OF DRAWINGS

Figure 1:
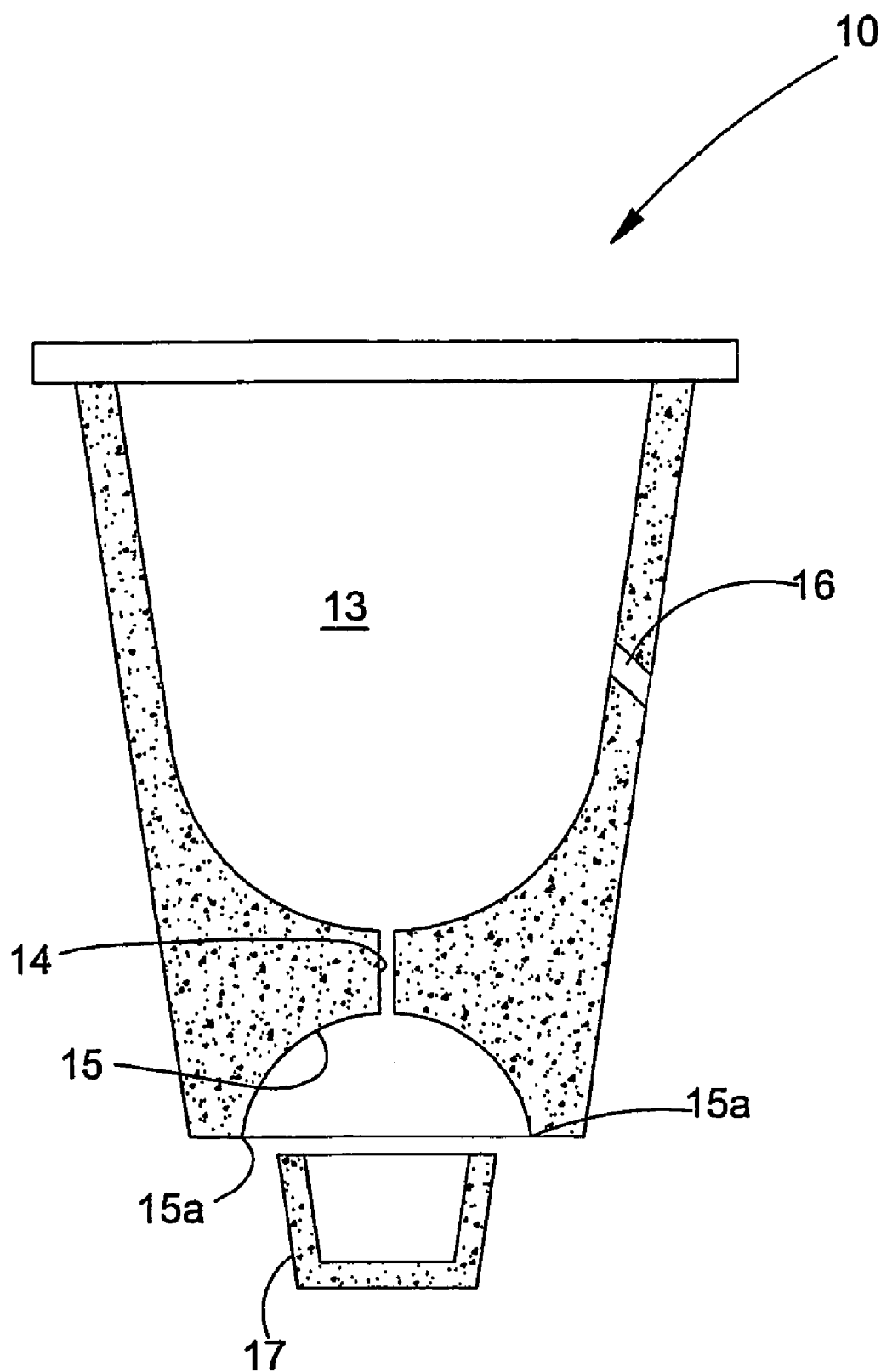
FIG. 1 is a schematic sectioned elevation of a separating vessel in accordance with the invention.
Figure 2:
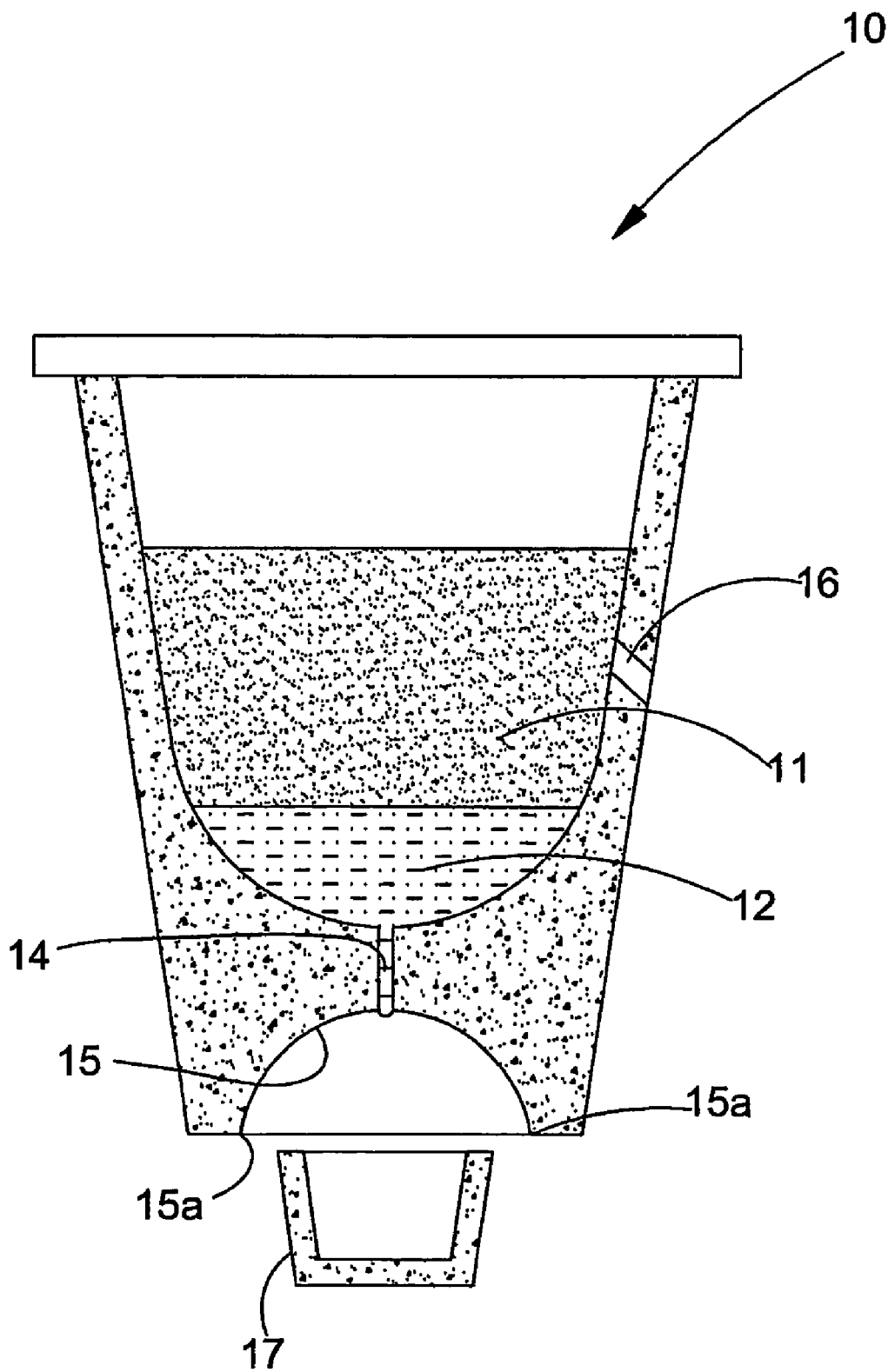
FIGS. 2 to 4 are schematic sectioned elevations of the separating vessel in FIG. 1, illustrating various steps in separating a molten slag from a molten collector material in fire forming part of a fire assay process.

Referring to the drawings, the invention provides a novel separating vessel 10 for separating molten slag 11 from molten collector material 12 for example in a fire assay process.

The separating vessel 10 comprises a container having an interior receiving zone 13 for the molten materials 11, 12, as shown in FIG. 1.

The vessel 10 of the invention further includes a low level outlet aperture 14 which is of a relatively small diameter, and will permit the collector material 12 to drain through such aperture 14 by gravity, while the molten slag 11 will substantially be prevented from passing through the aperture 14 as a result of the higher viscosity and/or lower density of the molten slag 11.

Figure 3:
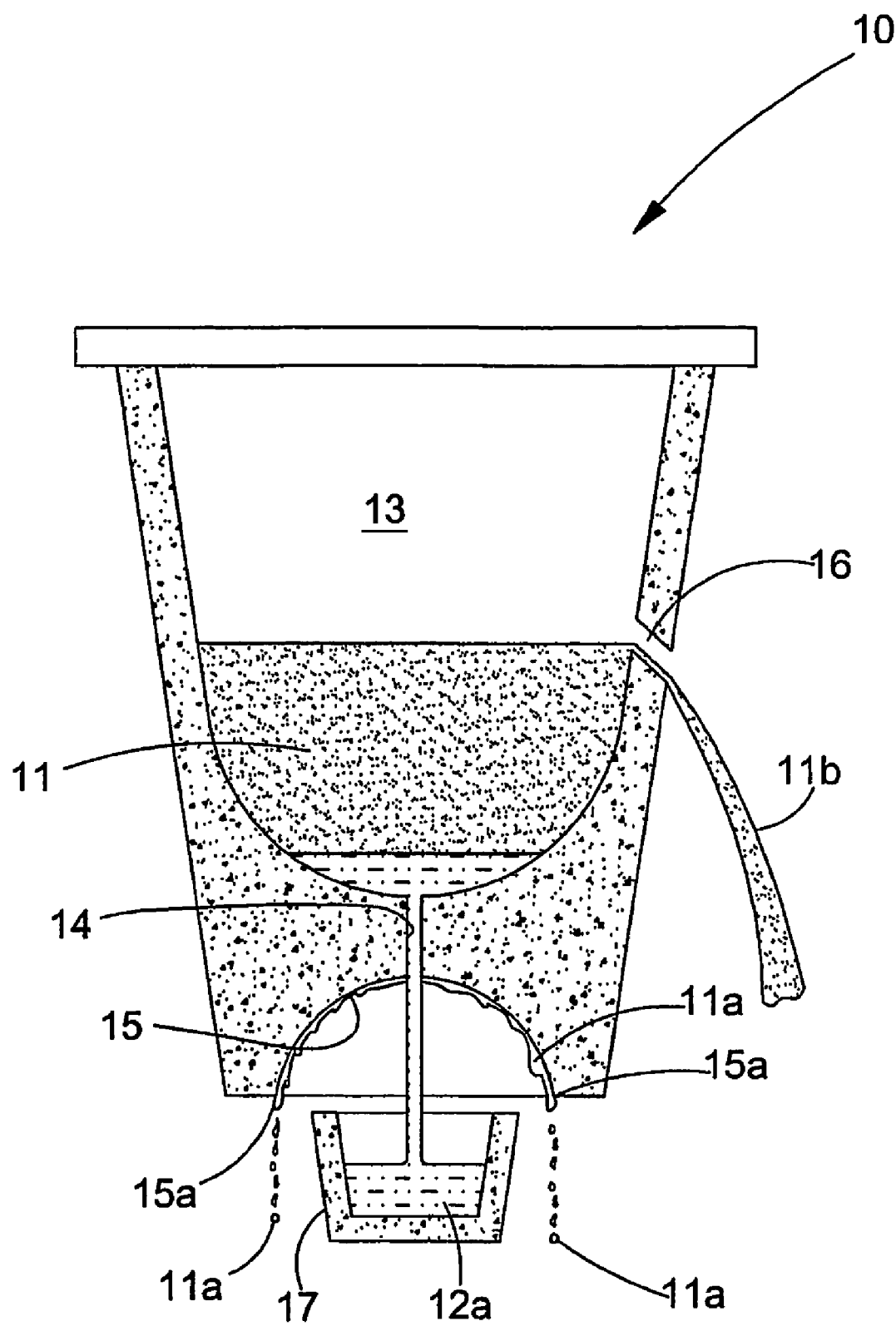
Figure 4:
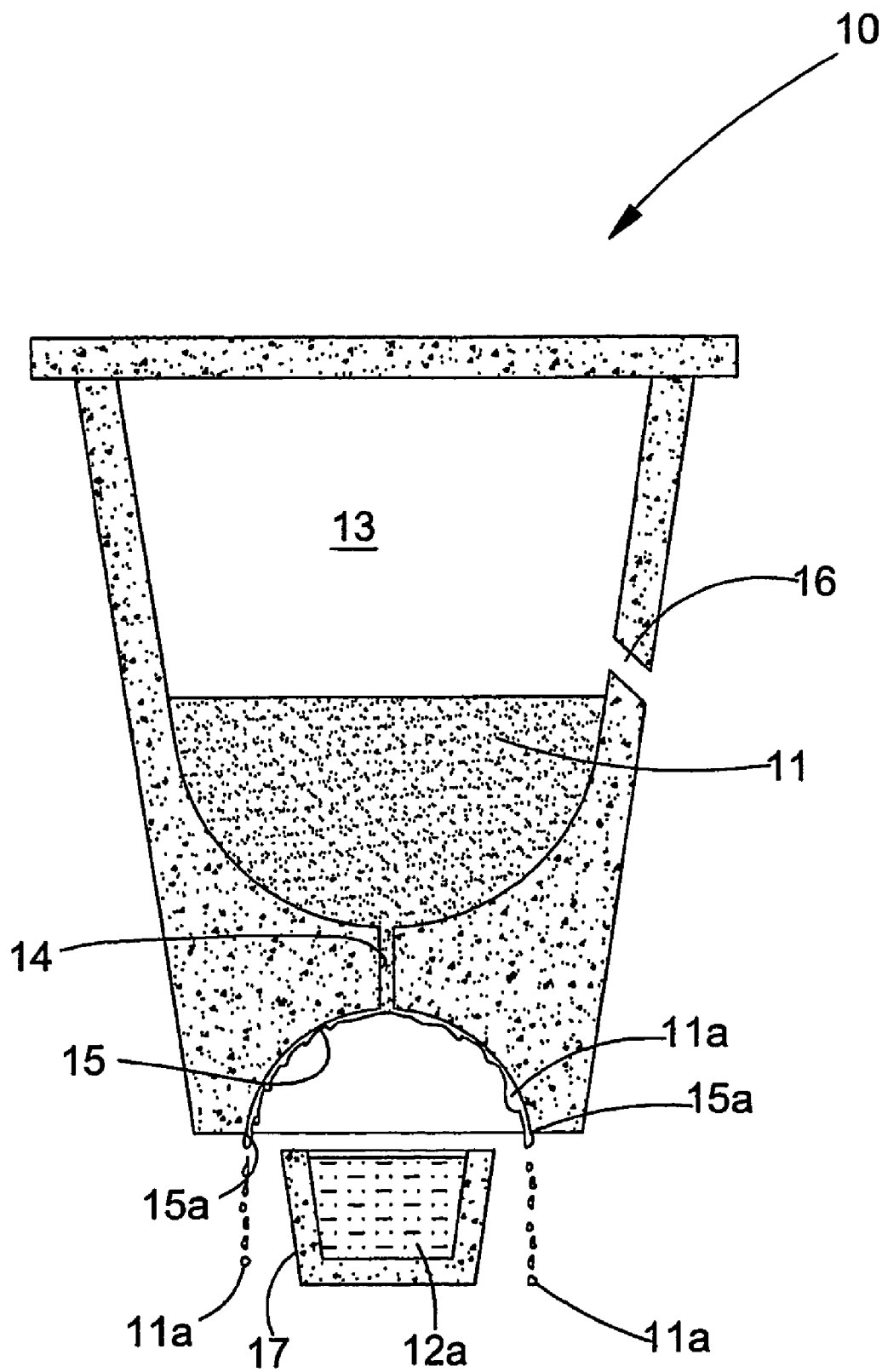

It is a feature of the invention that a separation surface 15 is provided on the exterior of the container 10 in the zone of the outlet aperture 14, such separation surface 15 being adapted to separate any molten slag 11a which may trickle through the outlet aperture 14, from the molten collector material 12a, FIG. 3 and FIG. 4.

In the arrangement illustrated, this separating surface 15 is in the form of a concave surface which is concentrically arranged relative to the axis of the outlet aperture 14. It has been found that with the arrangement of the invention, molten slag droplets 11a tend to cling to the concave surface 15, and are carried laterally away from the outlet aperture 14 ultimately to gather at a rim 15a of the concave surface from which they drop downwardly under the force of gravity, FIG. 3. This behaviour of the molten slag droplets 11 a can be ascribed to the low density of the slag material 11 and/or its surface tension. The collector material 12a, FIG. 3, on the other hand having different physical characteristics in respect of density and surface tension tends to pour directly vertically downwardly from the exit of the outlet aperture 14 under the force of gravity.

In the arrangement illustrated, the molten collector material 12a is collected in a collection vessel 17, while the molten slap drops 11a are transported laterally beyond the collection vessel 17 for separate collection.

A further feature of the invention comprises an intermediate outlet 16 for molten slag 11 in the side wall of the container 10 in a position spaced vertically upwardly from the outlet aperture 14 for collector material 12. The purpose of this intermediate slag outlet 16 is to drain the majority of molten slag 11 from the separating container while the molten collector material 12 is being drained through the outlet aperture 14. The relatively small portion of slag 11 which ultimately remains in the separation vessel 10 after draining of the collector material 12 can thus readily be removed from the container 10 by inversion thereof, or tilting thereof, not shown.

Thus in use, for example in a fire assay process for determining the concentration of PGM's (Platinum Group Metals) in an ore sample, such ore sample will be comminuted and mixed with a flux material, and introduced into a reaction vessel. The flux will be caused to fuse to produce a molten slag and a molten collector material such as lead, silver, etc, which acts to collect the PGM's. The molten mixture is then introduced into the separating vessel 10 of the invention in order to separate the molten collector material 12 from the molten slag 11 as described above. In certain cases the separating vessel 10 of the invention could also act as the reaction vessel.

It has been found that with the method described above, sufficient and effective separation of the molten slag 11 and molten collector material 12 can be achieved to enable further analysis of the collector material 12 and entrained PGM's.

Doubtless many variations are possible without departing from the principles set out in the consistory clauses. Thus, the separation surface 15 could for example merely comprise a surface which is angled to the vertical in a single plane or in several planes whereby molten slag drops 11a are carried transversely away from outlet duct 14 for separate collection. Alternatively, the separation surface 15 could be could be conical.

The invention claimed is:

1. A separating vessel suitable for use in the treatment of a mineral sample wherein a molten slag is separated from a molten collector material, the separating vessel comprising:
    a container defining an interior cavity for receiving the molten slag and the molten collector material,
    an outlet aperture leading from the interior cavity to the exterior of the container,
    a separating surface associated with the outlet aperture, the separating surface being shaped to cause droplets of slag to be carried along such surface, while droplets of collector material drip off such surface by the force of gravity, and
    a collection vessel for collecting the collector material dripping off of such surface, the separating surface extending beyond the collection vessel so that the slag being carried along such surface is carried beyond the collection vessel and thereby separated from the collector material.

2. A separating vessel according to claim 1 wherein the separating surface is a downwardly directed concave surface.

3. The separating vessel according to claim 2 wherein the concave surface is concentrically disposed relative to the outlet aperture.

4. The separating vessel according to claim 1 wherein the outlet aperture has dimensions such that the collector material passes through the aperture under the force of gravity, while the molten slag is substantially prevented from passing through the outlet aperture, so that the majority of molten slag will be arrested at the outlet aperture, but a small portion of the molten slag may pass through the outlet aperture.

5. A separating vessel suitable for use in the treatment of a mineral sample wherein a molten slag is separated from a molten collector material, the separating vessel comprising:
    a container defining an interior cavity for receiving the molten slag and the molten collector material,
    an outlet aperture leading from the interior cavity to the exterior of the container, and
    a separating surface associated with the outlet aperture, the separating surface being shaped to cause droplets of slag to be carried along such surface, while droplets of collector material drip off such surface by the force of gravity,
    wherein the outlet aperture is disposed at low level in the interior cavity, and
    a slag outlet is provided in the container spaced vertically upwardly from the outlet aperture so that at least a portion of the molten slag overlying the collector material in the molten state drain from the slag outlet during the process of draining the collector material through the outlet aperture.

6. A method of separating molten collector material from molten slag suitable for use in the treatment of a mineral sample, the method comprising the steps of:
    providing the separating vessel claimed in claim 1,
    introducing a mixture of molten slag and molten collector material into the vessel, whereby the slag settles above the collector material as a result of density differentials;
    draining the collector material through the outlet aperture under the force of gravity while the slag is substantially arrested by the outlet aperture;
    further separating the collector material from the slag which has passed through the outlet aperture at the separating surface, where the collector material drips generally vertically downwardly from the exit of the outlet aperture under the force of gravity into the collection vessel, while the slag is carried along the separating surface beyond the collection vessel and thereby separated from the collector material.

7. A method of separating molten collector material from molten slag suitable for use in the treatment of a mineral sample, the method comprising the steps of:
    providing a separating vessel comprising:
        a container defining an interior cavity for receiving the molten slag and the molten collector material,
        an outlet aperture leading from the interior cavity to the exterior of the container,
        a separating surface associated with the outlet aperture, the separating surface being shaped to cause droplets of slag to be carried along such surface, while droplets of collector material drip off such surface by the force of gravity,
    introducing a mixture of molten slag and molten collector material into the vessel, whereby the slag settles above the collector material as a result of density differentials;
    draining the collector material through the outlet aperture under the force of gravity while the slag is substantially arrested by the outlet aperture;
    further separating the collector material from the slag which has passed through the outlet aperture at the separating surface, where the collector material drips generally vertically downwardly from the exit of the outlet aperture under the force of gravity into the collection vessel, while the slag is carried along the separating surface beyond the collection vessel providing a slag outlet vertically upwardly spaced from the collector material outlet and draining slag through the slag outlet.

8. The method according to claim 7 wherein slag is drained through the slag outlet during or prior to draining the collector material through the collector material outlet aperture.

9. The separating vessel according to claim 1 wherein the outlet aperture is disposed at low level in the interior cavity, and a slag outlet is provided in the container spaced vertically upwardly from the outlet aperture so that at least a portion of the molten slag overlying the collector material in the molten state drains from the slag outlet during the process of draining the collector material through the outlet aperture.

10. The method according to claim 6 further comprising the steps of providing a slag outlet vertically upwardly spaced from the collector material outlet and draining slag through the slag outlet.

11. The method according to claim 10 wherein the slag is drained through the slag outlet during or prior to draining the collector material through the collector material outlet aperture.

* * * * *